United States Patent [19]

Rupp

[11] Patent Number: 5,463,100
[45] Date of Patent: Oct. 31, 1995

[54] PROCESS FOR THE PREPARATION OF AMINOARYL β-SULFATOETHYL SULFONE COMPOUNDS

[75] Inventor: Walter Rupp, Kriftel, Germany

[73] Assignee: Hoechst Aktiengesellschaft, Germany

[21] Appl. No.: 301,311

[22] Filed: Sep. 6, 1994

Related U.S. Application Data

[63] Continuation of Ser. No. 827,561, Jan. 27, 1992, abandoned, which is a continuation of Ser. No. 499,392, filed as PCT/EP88/01081 Nov. 29, 1988, abandoned.

[30] Foreign Application Priority Data

Dec. 11, 1987 [DE] Germany .......................... 37 42 044.5
Jul. 1, 1988 [DE] Germany .......................... 38 22 231.0

[51] Int. Cl.$^6$ .................................................. C07C 305/18
[52] U.S. Cl. ................................................ 558/29; 558/25
[58] Field of Search ........................................ 558/29, 25

[56] References Cited

U.S. PATENT DOCUMENTS

| | | | |
|---|---|---|---|
| 3,135,779 | 6/1964 | Hoyer et al. ........................... | 558/29 |
| 4,334,076 | 6/1982 | Steuernagel et al. ................. | 548/375 |
| 4,346,046 | 8/1982 | Nishimura et al. .. | |
| 4,482,501 | 11/1984 | Nishimura et al. .. | |

FOREIGN PATENT DOCUMENTS 45-36492R  11/1970  Japan ..................................... 558/29

OTHER PUBLICATIONS

Weissberger, *Separation and Purification*, Part I, pp. 821–822, (1956).

*Primary Examiner*—Johann Richter
*Assistant Examiner*—John Peabody

[57] ABSTRACT

Aminoaryl β-sulfatoethyl sulfone compounds, such as, for example 4-(β-sulfatoethylsulfonyl)-aniline, can be prepared in a quick and easy manner from their corresponding β-hydroxyethyl sulfone compounds by sulfation by spraying a solution or suspension or paste of this aminoaryl β-hydroxyethyl sulfone compound or the acylamino compound thereof in sulfuric acid or aqueous sulfuric acid into a hot inert gas stream of a convection dryer. In this procedure, the drying, esterification reaction and the hydrolysis of any acylamino group present takes place synchronously. The sulfato compound is preferably obtained in the form of granules.

19 Claims, 3 Drawing Sheets

PROCESS FOR THE PREPARATION OF AMINOARYL β-SULFATOETHYL SULFONE COMPOUNDS

CROSS REFERENCE TO RELATED APPLICATIONS

This application is a continuation of application Ser. No. 07/827,561, filed Jan. 27, 1992, now abandoned, which is a continuation of Ser. No. 07/499,392, filed as PCT/EP88/01081 Nov. 29, 1988, now abandoned.

The invention is in the technical field of the synthesis of intermediates, in particular for fiber-reactive dyes.

Aminoaryl β-sulfatoethyl sulfone compounds are nowadays prepared industrially mainly via two process variations by sulfation of the corresponding aminoaryl β-hydroxyethyl sulfone compound or acylamino derivatives thereof, such as the acetylamino compound thereof, by means of a sulfating agent such as, for example, concentrated aqueous sulfuric acid or 100% strength sulfuric acid or sulfuric acid containing sulfur trioxide with simultaneous hydrolysis of any acylamino group which may be present (see also Angewandte Chemie 74, 966 (1962)).

In one process variation, the amino- or acylaminoaryl β-hydroxyethyl sulfone compound is stirred into excess, about 95 to 96% strength by weight or 100% strength by weight sulfuric acid or oleum having a different content of free sulfur trioxide at room temperature or slightly elevated temperature such as, for example, at a temperature between 35° and 50° C. Usually, a sulfuric acid excess of up to 1,000 mol % is used, which simultaneously functions as a solvent and for binding water of the reaction. This process has various disadvantages. If the esterification product is precipitated by dilution with water and ice either as an inner salt or, after neutralization, as a neutral salt, in either case waste water having a high salt pollution is formed in the process. If the esterification product is further processed in solution, such as, for example, for the preparation of azo dyes in a diazotization reaction, the esterification reaction and the preparation of the dye have to be coordinated in the course of the production in terms of time. Neutralization of the dye solutions, such as, for example, by means of sodium carbonate, sodium hydroxide solution or calcium carbonate produces substantial amounts of salt which crystallize as sodium sulfate hydrate (Glauber salt) from the dye solutions at Low temperatures or are precipitated as calcium sulfate and have to be further utilized or stored in a sanitary landfill.

In the other process variation, the esterification is carried out using stoichiometric amounts of sulfuric acid or an excess of 2 to 30 mol % of sulfuric acid in a so-called contact dryer such as, for example, in a drying pan, at a temperature between about 120° C. and about 150° C. Other apparatuses, by means of which it was proposed to carry out these reactions, are heated kneaders and conveyor dryers. The aminoaryl β-hydroxyethyl sulfone starting compound or the acetylamino derivative thereof is usually dried and stirred into sulfuric acid monohydrate or concentrated sulfuric acid. The entire mixture is then heated to the optimum reaction temperature for the particular product, and the water of the reaction and the acetic acid liberated are driven off at atmospheric pressure or reduced pressure. During this process, the esterification product is obtained in solid form. This procedure too has disadvantages. Thus, long reaction times of several hours are necessary for this due to the poor heat transfer from the heated areas of the reactor into the material of the product, in particular if this material has reached the solid phase. The grade of the product is adversely affected by the formation of byproducts caused by the stationary excessive thermal stress in conjunction with the long reaction times. Before reaching the solid state, the reaction mixture possibly—as a function of the particular starting aminoaryl β-hydroxyethylsulfone— passes through a highly viscous phase subjecting the apparatuses to a high mechanical stress, which in turn leads to a greater need for repairs. In addition, the reactors used for this purpose and usually manufactured from austenitic steels become highly corroded by diluted sulfuric acid such as 20 to 80% strength by weight sulfuric acid at temperatures above 120° C., during which a wall corrosion rate of up to 10 mm per year can occur. The final products formed have an inhomogeneous particle size distribution, that is, simultaneously powder and agglomerates in lump form, which require an additional comminution in crushers or mills. Furthermore, it is a disadvantage for their further processing that the esterification products obtained as inner salts are produced in a mechanically hard form and require long reaction times when dissolved in water by neutralization with alkaline agents.

Furthermore, German Offenlegungsschrift No. 3,026,808 discloses processes in which the esterification is carried out using a small excess of sulfuric acid and the removal of the volatile reaction products is carried out azeotropically using organic solvents or by evaporation from the kneaded mixture at atmospheric pressure or under reduced pressure or in driers by hot-air circulation. The reaction times in this procedure are at least 4 hours (for example Examples 39 and 48) and furthermore, as a rule, auxiliaries such as diatomaceous earth, are added, which again have to be removed from the final product. The essential feature of this known process of German Offenlegungsschrift No. 3,026,808 is that the esterification in the aqueous sulfuric acid is carried out either initially at temperatures around 90° to 125° C. and then the water is removed in an evaporator (for example Examples 37, 40, 48 and 54) or that during the esterification period which lasts several hours the water is slowly removed in a circulation drier (for example Example 39). In addition to these disadvantages, namely a long reaction time and moreover, as a rule, a high excess of sulfuric acid, these procedures, due to the highly corrosive nature of the aqueous sulfuric acid at the temperatures used, require apparatuses manufactured from extremely high-quality materials; commercially available stainless steels are corroded under these conditions.

By means of the present invention it has now been found that the abovementioned disadvantages of the known procedures can surprisingly be avoided and the esterification reaction and simultaneous drying can be carried out using small amounts of sulfuric acid, if the sulfating reaction of aminoaryl β-hydroxyethyl sulfone compounds or the acylamino derivatives thereof are carried out in such a manner that a solution or suspension or paste of this aminoaryl β-hydroxyethyl sulfone compound or the acylamino compound thereof in 100% sulfuric acid or in aqueous sulfuric acid having a water content of up to 80% by weight in a molar ratio of the β-hydroxyethylsulfonyl starting compound to $H_2SO_4$ of 1:1 to 1:1.05 after its preparation is sprayed into the hot gas stream (air, inertized air, nitrogen) of a fluidized bed spray granulator or a spray dryer or a spray dryer having an integrated fluid bed and the drying, the esterification reaction and the hydrolysis of any acylamino group which may be present are carried out synchronously at a temperature between 100° and 200° C., preferably between 110° and 180° C.

As can be seen from the above details, the sulfuric acid can be used in a stoichiometric amount; preferably, it is used in the excess amount given. Even at this slight excess of sulfuric acid, complete esterification by means of the procedure according to the invention is ensured and a solution or suspension or paste processible by spraying can be produced from the starting compound under (sic) sulfuric acid, which are preferably prepared at 80° to 115° C.

The abovementioned apparatuses employed according to the invention are referred to below as convection dryers. Such convection dryers have been described numerous times in the literature such as, for example, in Verfahrenstechnik 10, 758–763 (1976), in Chem. Ing. Techn. 51, 266–277 (1979) and Chem. Ing. Techn. 59, 112–117 (1987). The convection dryers used according to the invention are usually those apparatuses which are conventionally used in industry, such as, for example, fluidized bed spray granulators in which the fluidized bed is produced pneumatically and/or mechanically, fluid bed dryers, spray dryers and also spray dryers having an external or integrated fluid bed and spin flash dryers.

According to the invention, preference is given to the use of fluidized bed spray granulators, spray dryers and spray dryers having an integrated fluid bed. Schematic diagrams of the operation by which the process according to the invention can be carried out using these convection dryers can be seen from the accompanying FIGS. 1, 2 and 3.

Figure 1:
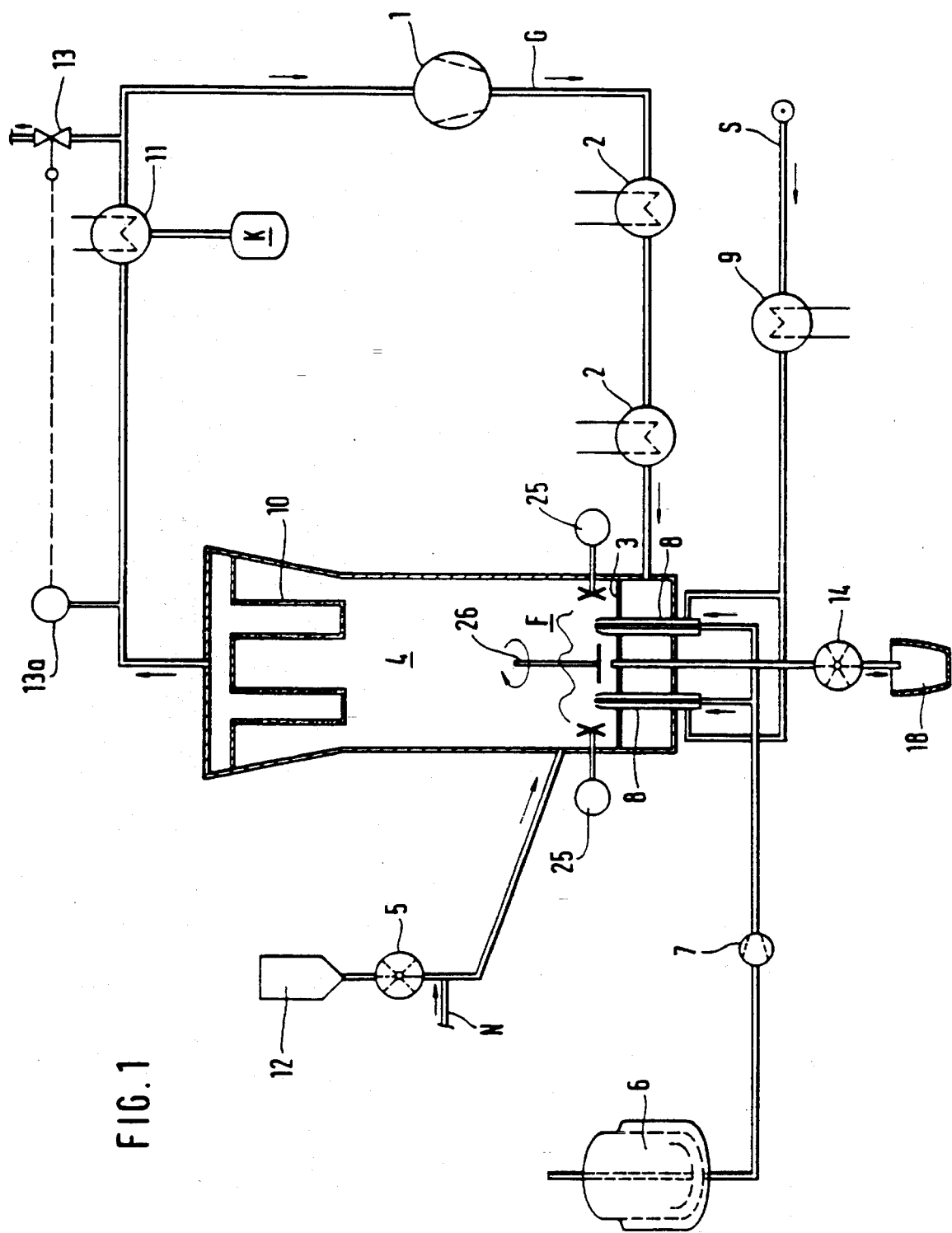
FIG. 1=schematic diagram of the operation of a fluidized bed spray granulator.

In these figures, the symbols have the following meanings:
(1)=Ventilator
(2)=Gas heater
(3)=Sieve plate
(4)=Fluidized bed spray granulator
(5)=Star wheel
(6)=Container for the starting reaction mixture
(7)=Pump
(8)=Atomizing nozzle (one-component or two-component nozzle) or atomizing disk
(9)=Gas heater
(10)=Dust filter
(11)=Condenser
(12)=Container for "fine final product" (sulfato final product)
(13)=Means for maintaining pressure with pressure control (13a)
(14)=Star wheel
(15)=Spray dryer
(16)=Cyclone
(17)=Gas washer
(18)=Collection vessel for granules (final product)
(19)=Gas heater
(20)=Spray dryer having an integrated fluid bed
(21)=Fine final product feed
(22)=Discharge of the gas through the tower ceiling
(23)=Slide valve
(24)=Fine final product inlet
(25)=Crusher
(26)=Stirrer
(F)=Fluid bed
(G)=Gas (heat carrier gas; drying and/or fluidizing gas)
(N)=Carrier gas
(S)=Spray gas
(K)=Condensate.

The gases used are usually air or nitrogen or an air/nitrogen mixture preferably having a low oxygen content. The drying and the esterification reaction and also the hydrolysis of any acylamino group which may be present are usually carried out between 100° and 200° C., preferably between 110° and 180° C. The temperatures are usually set by the spraying rate of the reaction mixture into the hot gas stream and are kept constant. The entry temperature of the gas (G) is usually between 150° and 360° C., preferably between 180° and 300° C. The choice of the gas entry temperature can be a function, for example, of the choice of the convection dryer used and/or of the amount of the volume stream chosen of the gas and/or of the spraying rate and concentration of the reaction mixture. The maximum gas entry temperatures mentioned in the examples are temperatures used in the experiments, and do not represent any limitation for the technical procedure using the individual apparatuses.

The sulfuric acid can be used in a stoichiometric amount; preferably it is used in a small excess, relative to the β-hydroxyethylsulfonyl starting compound, such as, for example, in an up to 15% strength molar excess. Preferably the molar ratio of β-hydroxyethylsulfonyl starting compound to $H_2SO_4$ is in the range from 1:1 to 1:1.05, even in this case complete esterification being guaranteed and it being possible to prepare a solution or suspension or paste from the starting compound and sulfuric acid, which solution, suspension or paste can be processed by spraying; preferably the solutions are prepared at 80° to 115° C.

The sulfuric acid used can be not only 100% strength but also aqueous sulfuric acid having a water content of up to 90% by weight, depending on whether the starting compound is used as dry technical grade or water-moist technical grade material. Usually aqueous sulfuric acid having a concentration of more than 20% by weight of $H_2SO_4$ is used; to avoid the separate drying of the starting compound, the starting compound is preferably used as technically water-moist having a solids content of 50 to 95% by weight, as it is formed in the preparation process, and sulfuric acid having a concentration of 35 to 95% by weight of $H_2SO_4$ is used and the drying and the esterfication reaction are carried out in one step. The concentrations of β-hydroxyethylsulfonyl starting compound and sulfuric acid in the solutions, pastes or suspensions are variable, if the molar ratio of β-hydroxyethylsulfonyl starting compound to sulfuric acid is maintained up to 1:1.15 or preferably up to 1:1.05.

According to the invention, the procedure is usually such that starting from a solution, suspension or paste of the amino- or acylamino-aryl β-hydroxyethyl sulfone starting compound in sulfuric acid, this compound is introduced into the reactor by means of a pump and is atomized there by means of a nozzle or atomizing disk into the hot gas stream (G). Due to the large product surface area formed, this causes an immediate hydrolytic elimination of the acyl group and simultaneous complete drying and esterification (sulfation) to give the reaction product. Advantageously, the reaction mixture is fed into the gas stream in such a manner that, if the design of the reaction apparatus allows it, a fluid bed of the sulfato end product is formed in the streaming gas. The formation of a fluid bed leads to the advantage that the atomized reaction mixture coats the fine final product of the fluid bed with a thin layer or that the fine particles agglomerate and thus produce dust-free granules. The formation of granules having particle sizes between, for example, 100 and 3,000 μm is regulated, if necessary, by means of metering of the fine final product and/or crusher. The granules can be discharged from the reaction apparatus and be separated by appropriate separating means into particle sizes as desired. Very fine particles ("fines") and/or comminuted coarser agglomerates ("oversize") can be reintroduced into the reaction apparatus or the fluid bed of the reaction apparatus to obtain the final product in the desired particle size. The water evaporating from the materials used and from the reaction is discharged together with the eliminated acid of any acyl group which may be present, for example acetic acid from the acetyl group, by means of the hot gas stream and precipitated in condensers by cooling. The gas freed from the condensate is again heated to the required entry temperature and again introduced into the reactor as heat carrier gas. The fluid bed temperature or the gas exit temperature in spray dryers is established, for example, by the metering rate of the reaction mixture and kept constant.

It was surprising and not forseeable that in the temperature range between 100° and 200° C. very short stationary residence times are sufficient for the reaction to obtain a synchronous course of the water evaporation from the sprayed reaction mixture and a complete esterification reaction. Thus it is possible to discharge reaction product from the reactor at the same rate at which the starting reaction mixture is sprayed in. As a result, the reaction according to the invention can be carried out continuously. It produces a final product having a high degree of esterification and a high product grade by virtue of suppressing the formation of byproducts, which final product is additionally obtained directly as a conditioned product, that is, fine granules without or without any significant pollution by dust and has much improved properties for its further processing, such as, for example, easier wettability by water and a higher dissolution rate in water upon neutralization by means of alkalis of the sulfato compounds present as inner salts.

The present invention relates in particular to the preparation of an aminoaryl β-sulfatoethyl sulfone compound conforming to the general formula (1)

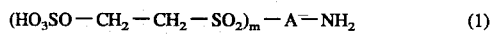

$$(HO_3SO-CH_2-CH_2-SO_2)_m-A-NH_2 \qquad (1)$$

in which m denotes the number 1 or 2 and A is a phenylene or naphthylene radical, both of which can be substituted by 1, 2 or 3, preferably 1 or 2, substituents from the group consisting of alkyl of 1 to 4 carbon atoms such as methyl and ethyl, alkoxy of 1 to 4 carbon atoms such as methoxy and ethoxy, halogen such as fluorine and in particular bromine and chlorine, carboxyl and hydroxyl, by using the corresponding starting compound of the general formula (2)

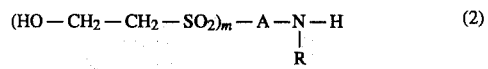

$$(HO-CH_2-CH_2-SO_2)_m-A-\underset{R}{N}-H \qquad (2)$$

in which m and A have the abovementioned meanings and R stands for a hydrogen atom or an acyl group, in particular of a lower alkanecarboxylic acid, such as the acetyl group. Preferably, the process is used for sulfation of compounds of the general formula (2) in which m is the number 1 and A denotes a 1,3- or 1,4-phenylene radical which is unsubstituted or substituted by 1 bromine atom or by 1 or 2 methoxy groups or by 1 methyl group and 1 methoxy group, or A denotes a naphthylene radical, preferably 2,6- or 2,8-naphthylene radical.

Starting compounds conforming to the general formula (2) which can be converted according to the invention to sulfuric acid half esters thereof (sulfato compounds) are for example 4-(β-hydroxyethylsulfonyl)aniline, 3-(β-hydroxyethylsulfonyl)aniline, 2-methoxy-5-(β-hydroxyethylsulfonyl)aniline, 4-methoxy-5-(β-hydroxyethylsulfonyl)aniline, 2-hydroxy-5-(β-hydroxyethylsulfonyl)aniline, 2-methoxy-5-methyl-4-(β-hydroxy ethylsulfonyl)aniline, 2,5-dimethoxy-4-(β-hydroxyethyl sulfonyl)aniline, 2-bromo-4-(β-hydroxyethylsulfonyl)aniline, 6-(β-hydroxyethylsulfonyl)- 2-aminonaphthalene and 8-(β-hydroxyethylsulfonyl)- 2-aminonaphthalene and N-acetyl derivatives thereof.

The examples which follow serve to illustrate the invention. The parts mentioned and the percentages are by weight, unless stated otherwise. Parts by volume relate to parts by weight as the liter relates to the kilogram.

EXAMPLES

Figure 2:
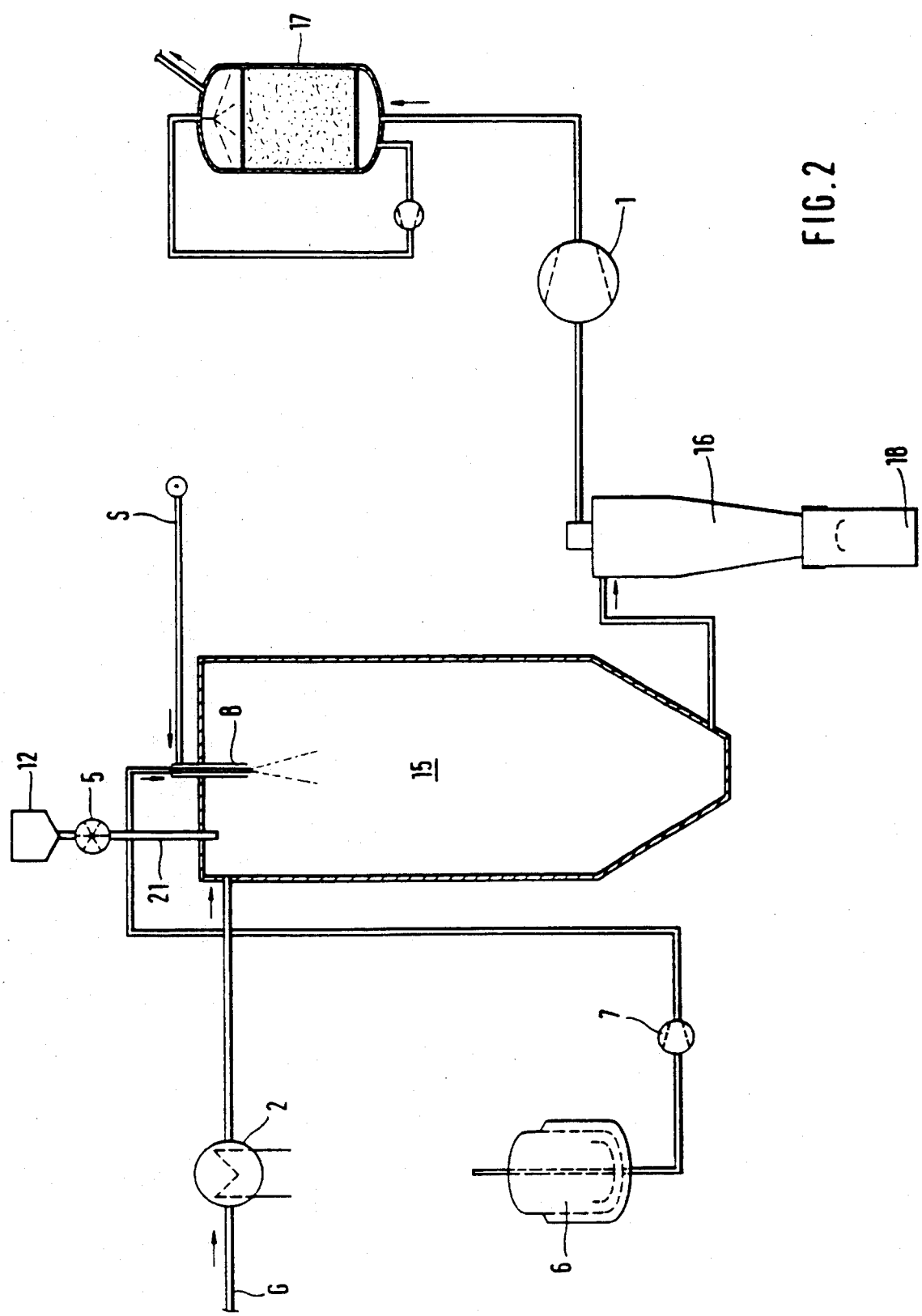
FIG. 2=schematic diagram of the operation of a spray dryer.
Figure 3:
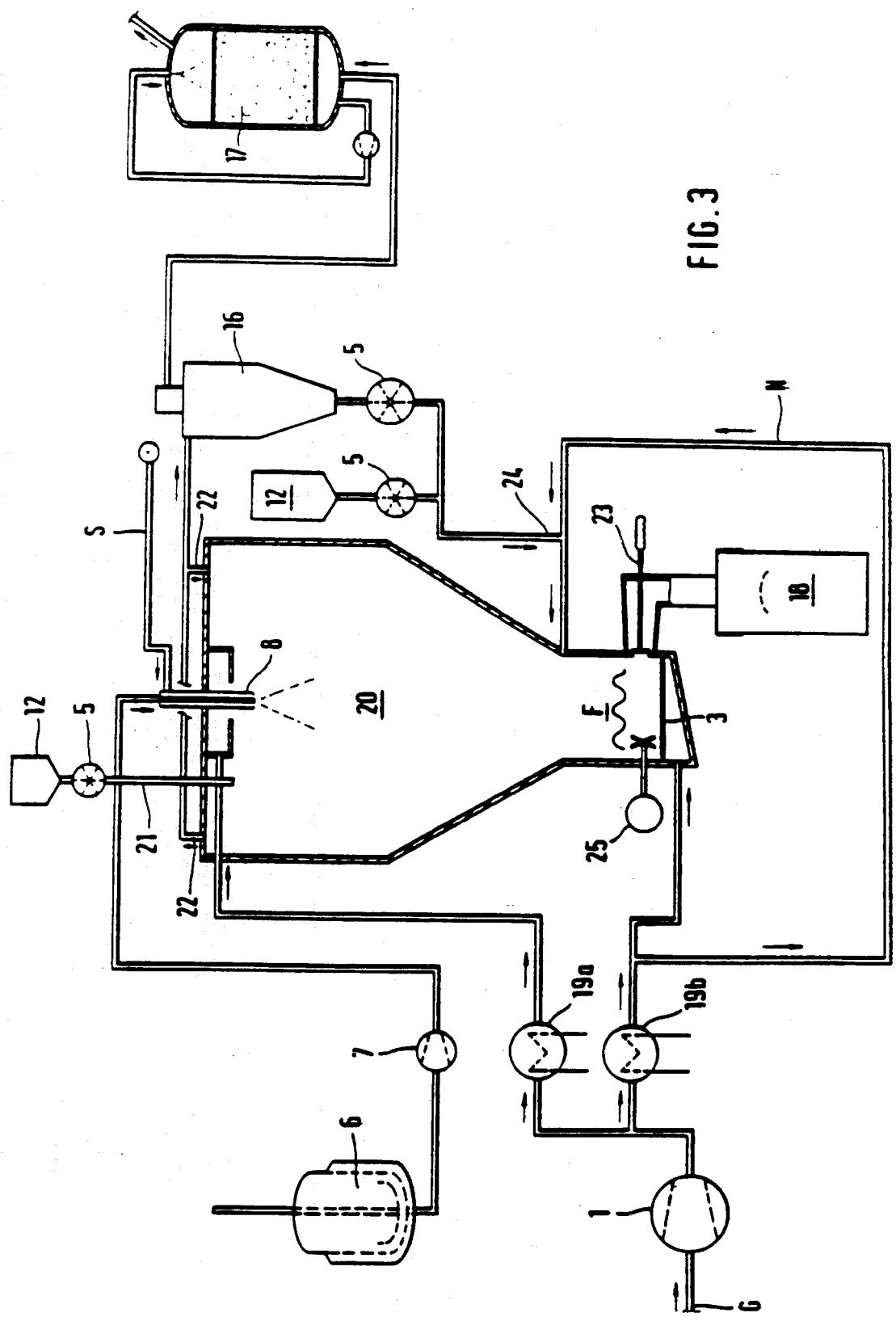
FIG. 3=schematic diagram of the operation of a spray dryer having an integrated fluid bed.

The procedure of the process according to the invention is illustrated in the examples which follow by means of the schematic diagrams of the operation described in the accompanying FIGS. 1, 2 and 3. These schematic diagrams of the operation merely represent illustrative examples and are as such not an essential part of the process according to the invention.

Principle of Operation of the Fluidized Bed Spray Granulator (FIG. 1)

Ventilator (1) conveys the gas (G) through the gas heaters (2), which can be heated, for example, electrically and/or by hot steam and/or by gas or oil burner, and through the sieve plate (3), above which the fluid bed (F) desired for the reaction is formed, which, if desired, can be additionally agitated by a stirrer (26), into granulator (4). First, finely milled final product, that is the aminoaryl-β-sulfatoethylsulfone compound, hereinafter designated as "fine final product", and/or an inert fine material, for example activated carbon, silicas or salts such as sodium sulfate, are initially introduced via the star wheel (5) and/or by blowing them in with a carrier gas (N) from container (12) into the fluid bed (F) to create, together with the hot fluidizing gas (=gas G) a fluid bed. Once the fluid bed has reached the reaction temperature of at least 100° C., the sulfuric acid solution, suspension or paste of the aminoaryl β-hydroxyethyl sulfone starting compound is conveyed from container (6) by means of pump (7) via the two-component nozzles (8) into the granulator (4) and atomized by means of spray gas S, which, if necessary, is heated in a gas heater (9), for example, to 90° C. The atomized reaction mixture coats the initially introduced, finely milled fine final product in the fluid bed with thin Layers so that drying and reaction can proceed at maximum rate due to the Large, always renewed surface area. During this step, the hot fluidizing gas takes up water and any volatile byproducts present from the reaction. It is purified from product dust in the dust filter (10), freed from water and volatile cleavage products in condensor (11) and reintroduced into the process through ventilator (1) and gas heaters (2). The spray gas which constantly flows into the process is automatically discharged through a means for maintaining pressure (13). The final product obtained is removed in the form of granules from the granulator (4) through the star wheel (14). Granules having a narrow particle size spectrum can be prepared selectively by introducing, for example parallel to the spraying in of the reaction mixture, fine final product from container (12) into the fluid bed or by producing fine final product in the fluid bed by means of the crusher (25) by allowing the crusher to operate in intervals or continuously.

Principle of Operation of the Spray Dryer (FIG. 2)

Hot gas (G) is sucked by means of a ventilator (1) via a gas heater (2) through the spray tower (15) and the cyclone (16) and subsequently injected into the gas washer (17) and purified there from fine dust and volatile reaction products. Simultaneously, the sulfuric acid solution, suspension or paste of the aminoaryl β-hydroxyethyl sulfone starting compound is conveyed from container (6), for example by means of pump (7), through the two-component nozzle (8) into the spray tower (15) and sprayed by means of the hot spray gas (S), which, if necessary, is heated, (instead of the two-component nozzle (8), a one-component nozzle or an atomizing disk can also be used). Simultaneously with the spraying in of the reaction mixture, fine final product can be introduced, if desired, from container (12) via star wheel (5) through the tower ceiling, The sprayed reaction mixture is freed in a cocurrent flow from water and any volatile byproducts of the reaction by means of the hot gas, conveyed into the cyclone (16) and there precipitated in container (18) in the form of granules. Fine dust particles of the final product which pass through the cyclone are washed out in the gas washer (17). At the bottom of the gas washer, an aqueous suspension of the β-sulfatoethyl sulfone final compound is formed, from which it can be isolated. By using a dust filter (10) and condenser (11), operation with recycling, as described in FIG. 1, is also possible. In this case, the gas washer can be omitted.

Principle of Operation of the Spray Dryer Having an Untegrated Fluid Bed (FIG. 3)

By means of a ventilator (1), the gas (G) is blown as a drying and reaction gas via the gas heater (19a) into the spray tower (20); furthermore the gas G is heated by the gas heater (19b) and injected via the sieve plate (3) as a fluidizing gas into the fluid bed (F) being formed. A bleed stream can be used as carrier gas for introducing fine final product, for example from cyclone (16) or a container (12), through a fine final product inlet (24) into the reactor (20), in particular into the fluid bed (F), in order to form a fluid bed at the beginning of the reaction or to control the particle size of the granules during the spraying, with or without the additional use of crusher (25). An optionally additional "powdering" with fine final product through the tower ceiling, can take place, for example, by means of the fine final product inlet (21) described in FIG. 2.

The sulfuric acid solution, suspension or paste of the aminoaryl β-hydroxyethyl sulfone starting compound is conveyed from container (6), for example by means of pump (7), into the two-component nozzle (8) of spray dryer (20) and is sprayed there by means of a spray gas (S), which, if desired, has been preheated. The resulting granules of the final product are discharged from the spray tower into container (18). The gas charged with water and any volatile byproducts of the reaction leaves the spray tower (20) via the tower ceiling (22) and is purified in cyclone (16) from not yet granulated final product and in the gas washer (17) from dust and volatile byproducts. The final product which is separated off in cyclone (16) from the gas stream in the form of fine final product can be reintroduced into the fluid bed for granulation via star wheel (5) and inlet (24).

EXAMPLES

1. Preparation of 4-(β-sulfatoethylsulfonyl)-aniline in a batchwise process

1.a Preparation of the reaction mixtures

Technical grade water-moist or technical grade dry 4-(β-hydroxyethylsulfonyl)-acetanilide is stirred into such an amount of aqueous sulfuric acid, for example, of 50 to 95% strength that the molar ratio between sulfonyl compound and sulfuric acid is, for example, 1:1 or 1:1.02 or 1:1.05 or 1:1.07. This gives, for example at 100° C., a solution, or at 20° to 25° C. a suspension which is fed into the convection dryer. Preferably those reaction mixtures are used which contain 50 to 66% of 4-(β-hydroxyethylsulfonyl)-acetanilide and 21 to 28% of sulfuric acid (calculated as 100% strength).

1.b Process examples

1.b.1 Process principle

In a fluidized bed spray granulator (for example in accordance with FIG. 1), a fluid bed is constructed by means of the gas (G) and the fine final product, that is, 4-(β-sulfatoethylsulfonyl)-aniline having a particle size, for example, smaller than or equal to 100 μm. The entry temperature of the gas (G) is chosen, for example, as described in Examples 1.b.2 to 1.b.5 and the fluid bed temperature (=reaction temperature) is kept constant as described in Examples 1.b.2 to 1.b.5 by continuously spraying one of the solutions or suspensions of the sulfonyl starting compound prepared in 1.a into the fluid bed. This produces granules in the fluid bed whose particle size is controlled by introducing fine final product of the sulfato compound and/or by crushing by means of crusher (25) and thus obtaining granules, for example, of. 100 to 800 μm or 100 to 2,000 μm or 100 to 3,000 μm. The process is interrupted, for example, after 2 or 3 or 4 or 5 hours, that is, as soon as the amount of granules in the fluid bed has become so large that the optimum "flow" of the granule particles can no longer be maintained. The fluid bed is then emptied, and the process starts again.

Example 1.b.2

The process is carried out, as described in process principle 1.b.1, using an entry temperature of the gas (G) of 200° C. and a fluid bed temperature (=reaction temperature) of 120° C. This gives granules having the composition and grade characteristics as described in 1.c.

Example 1.b.3

The process is carried out, as described in process principle 1.b.1, using an entry temperature of the gas (G ) of 200° C. and a fluid bed temperature (=reaction temperature) of 150° C. This gives granules having the composition and grade characteristics as described in 1.c.

Example 1.b.4

The process is carried out, as described in process principle 1.b.1, using an entry temperature of the gas (G) of 240° C. and a fluid bed temperature (=reaction temperature) of 170° C. This gives granules having the composition and grade characteristics as described in 1.c.

Example 1.b.5

The process is carried out, as described in process principle 1.b.1, using an entry temperature of the gas (G) of 170° C. and a fluid bed temperature (=reaction temperature) of 115° C. This gives granules having the composition and grade characteristics as described in 1.c.

1.c Results

On the basis of analyses of samples which were removed during the spraying of the sulfuric acid solution of the sulfonyl starting compound from the fluid bed, it was determined that the esterification reaction (sulfation) during the spraying proceeds spontaneously and virtually completely so that no afterreaction time ("heat treatment") is necessary. This is also confirmed by analyses of samples of granules which were subjected in the fluid bed at the reaction temperature chosen to a "heat treatment" of up to 4 hours and whose product composition with respect to the amount of sulfato final product underwent no more change. On average, the granules of Examples 1.b.2 to 1.b.5 contained 98% of 4-(β-sulfatoethylsulfonyl)-aniline, 0.1–0.5% of 4-(β-hydroxyethylsulfonyl)-acetanilide and 0.2–0.5% of 4-(β-hydroxyethylsulfonyl)-aniline.

The virtually dust-free granules are distinguished, compared with products which were prepared in contact dryers, for example a drying pan, by a higher dissolution rate in an aqueous suspension upon addition of anhydrous sodium carbonate up to a pH of 7.

2. Preparation of 4-(β-sulfatoethylsulfonyl)-aniline in a continuous procedure

2.a Preparation of the reaction mixtures

The reaction mixtures are prepared as described in 1.a.

2.b Process examples

As described in process principal 1.b.1, a fluid bed is constructed by means of the gas (G) and the fine final product of the sulfato compound. The entry temperatures of the gas (G) and the fluid bed temperatures used are chosen as described in Examples 1.b.2 to 1.b.4. In contrast to the procedure of the batch-wise preparation, in the continuous procedure the granules produced are removed parallel to the spraying of the reaction mixtures, as described in 1.a, continuously by means of the star wheel (14) so that the amount of granules present in the fluid bed remains constant. The particle size of the granules is controlled as in the batchwise procedure by metering in "fine final product" (sulfato compound) and/or by crushing the granules with the crusher (25) so that the process, owing to the constant amount of granules in the fluid bed and the constant particle size spectrum, takes place in the optimum "fluidized range". The continuous procedure used has been carried out for up to 98 hours without interruption.

2.c Results

Analyses and tests of the samples of granules removed first hourly then at longer intervals show the grade characteristics as described in 1.c.

3. Preparation of 4-(β-sulfatoethylsulfonyl)-aniline in a spray dryer (for example in accordance with FIG. 2)

3.a Preparation of the reaction mixtures

The reaction mixtures are prepared by stirring, as described in 1.a.

3.b Process examples

3.b.1 Process principle

The gas (G) is heated to the entry temperature, as described in Examples 3.b.2 to 3.b.5. The reaction mixtures which have been described in 1.a are continously sprayed into the hot gas stream at such a rate that the exit temperatures of the gas (G) described in Examples 3.b.2 to 3.b.5 remain constant. Simultaneously with the spraying of the reaction mixture "fine final product" (sulfato compound, particle size, for example, smaller than or equal to 100 μm) is channeled, if appropriate, from the container (12) by means of the star wheel (5) through the tower ceiling into the spray dryer.

Example 3.b.2

The process is carried out, as described in process principle 3.b.1, using an entry temperature of the gas (G) of 220° C. and a gas exit temperature of 150° C. This gives granules having the composition and grade characteristics as described in 1.c.

Example 3.b.3

The process is carried out, as described in process principle 3.b.1, using an entry temperature of the gas (G) of 260° C. and a gas exit temperature of 200° C. This gives granules having the composition and grade characteristics as described in 1.c.

Example 3.b.4

The process is carried out, as described in process principle 3.b.1, using an entry temperature of the gas (G) of 230° C. and a gas exit temperature of 180° C. This gives granules having the composition and grade characteristics as described in 1.c.

Example 3.b.5

The process is carried out, as described in process principle 3.b.1, using an entry temperature of the gas (G) of 200° C. and a gas exit temperature of 125° C. This gives granules having the composition and grade characteristics as described in 1.c.

4. Preparation of 4-(β-sulfatoethylsulfonyl)-aniline in a spray dryer having an integrated fluid bed (for example in accordance with FIG. 3)

4.a Preparation of the reaction mixtures

The reaction mixtures are prepared by stirring, as described in 1.a.

4.b Process examples

4.b.1 Process principle

The process proceeds as described in the principle of operation of the spray dryer having an integrated fluid bed. The drying and heat carrier gas is heated in the gas heater (19a) to the entry temperatures given in Examples 4.b.2 to 4.b.5. The fluidizing gas required for the fluid bed is heated in the gas heater (19b) to the fluid bed temperatures given in Examples 4.b.2 to 4.b.5. The temperature (exit temperature) of the gas stream (22) charged with volatile reaction products and product dust, which stream leaves the dryer through the tower ceiling, is adjusted, as described in Examples 4.b.2 to 4.b.5 and kept constant by metering (spraying) the reaction mixture at an appropriate rate continuously into the spray dryer. The size of the granules is controlled by introduction of "fine final product" (sulfato compound, particle size smaller than or equal to 100 μm) via the fine final product inlet (24) and/or the fine final product inlet (21) and/or by crushing with the crusher (25).

Example 4.b.2

The process is carried out, as described in process principle 4.b.1, using an entry temperature of the gas (G) of 300° C., a fluid bed temperature of 135° C. and a gas exit temperature of 150° C. This gives granules having the composition and grade characteristics as described in 1.c.

Example 4.b.3

The process is carried out, as described in process principle 4.b.1, using an entry temperature of the gas (G) of 350° C., a fluid bed temperature of 190° C. and a gas exit temperature of 200° C. This gives granules having the composition and grade characteristics as described in 1.c.

Example 4.b.4

The process is carried out, as described in process principle 4.b.1, using an entry temperature of the gas (G) of 260° C., a fluid bed temperature of 160° C. and a gas exit temperature of 160° C. This gives granules having the composition and grade characteristics as described in 1.c.

Example 4.b.5

The process is carried out, as described in process principle 4.b.1, using an entry temperature of the gas (G) of 210° C., a fluid bed temperature of 140° C. and a gas exit temperature of 160° C. This gives granules having the composition and grade characteristics as described in 1.c.

5. Preparation of 2-bromo-4-(β-sulfatoethylenesulfonyl)aniline in a batchwise procedure

5.a Preparation of the reaction mixtures

Technical grade water-moist or technical grade dry 2-bromo-β-(3-hydroxyethylsulfonyl)-aniline is stirred into such an amount of aqueous sulfuric acid, for example, of 30 to 95% strength that the molar ratio between sulfonyl compound and sulfuric acid is, for example, 1:1 or 1:1.02 or 1:1.05. This gives, for example at 80°–90° C., a solution, or at 20°–25° C., suspension which is fed into the convection dryer.

Preferably those reaction mixtures are used which contain 49–68% of 2-bromo-4-(β-hydroxyethylsulfonyl)aniline and 17.5–25% of sulfuric acid (calculated as 100% strength).

5.b Process examples

5.b.1 Process principle

In a fluidized bed spray granulator (for example in accordance with FIG. 1), a fluid bed is constructed by means of the gas (G) and the fine final product, that is, 2-bromo-4-(β-sulfatoethylsulfonyl)aniline having a particle size, for example, smaller than or equal to 100 μm. The entry temperature of the gas (G) is chosen, for example, as described in Examples 5.b.2 to 5.b.5 and the fluid bed temperature (=reaction temperature) is kept constant as described in Examples 5.b.2 to 5.b.5 by continuously spraying one of the solutions or suspensions of the sulfonyl starting compound prepared in 5.a into the fluid bed. This produces granules in the fluid bed whose particle size is controlled by introducing fine final product of the sulfato compound and/or by crushing by means of crusher (25) and thus obtaining granules, for example, of 100 to 800 μm or 100 to 2,000 μm or 100 to 3,000 μm. The process is interrupted, for example, after 2 or 3 or 4 or 5 hours, that is, as soon as the amount of granules in the fluid bed has become so Large that the optimum "flow" of the granule particles can no Longer be maintained. The fluid bed is then emptied, and the process starts again.

Example 5.b.2

The process is carried out, as described in process principle 5.b.1, using an entry temperature of the gas (G) of 200° C. and a fluid bed temperature (=reaction temperature) of 140° C. This gives granules having the composition and grade characteristics as described in 5.c.

Example 5.b.3

The process is carried out, as described in process principle 5.b.1, using an entry temperature of the gas (G) of 230° C. and a fluid bed temperature (=reaction temperature) of 160° C. This gives granules having the composition and grade characteristics as described in 5.c.

Example 5.b.4

The process is carried out, as described in process principle 5.b.1, using an entry temperature of the gas (G) of 170° C. and a fluid bed temperature (=reaction temperature) of 115° C. This gives granules having the composition and grade characteristics as described in 5.c.

Example 5.b.5

The process is carried out, as described in process principle 5.b.1, using an entry temperature of the gas (G) of 210° C. and a fluid bed temperature (=reaction temperature) of 130° C. This gives granules having the composition and grade characteristics as described in 5.c.

5.c Results

On the basis of analyses of samples Of granules which were removed during the spraying of the sulfuric acid solution or suspension of the sulfonyl starting compound from the fluid bed, it was determined that the esterification reaction (sulfation) during the spraying proceeds spontaneously and virtually completely so that no after reaction time ("heat treatment") is necessary. This was also confirmed by analyses of samples of granules which were subjected in the fluid bed at the reaction temperature chosen to a "heat treatment" of up to 2 hours and whose product composition with respect to the amount of sulfato final product underwent no more change. On average, the granules of Examples 5.b.2 to 5.b.5 contained 96–98% of 2-bromo-4-(β-sulfatoethylsulfonyl)aniline 1.5–2.5% of 2-bromo-4-(β-hydroxyethylsulfonyl)aniline and 1–1.5% of 4-(β-sulfatoethylsulfonyl)-aniline.

The virtually dust-free granules are distinguished, compared with products which were prepared in contact dryers, for example a drying pan, by a higher dissolution rate in an aqueous suspension upon addition of anhydrous sodium carbonate up to a pH of 7.

6. Preparation of 2-bromo-4-(β-sulfatoethylsulfonyl)aniline in a continuous procedure

6.a Preparation of the reaction mixtures

The reaction mixtures were prepared as described in 5.a.

6.b Process examples

As described in process principle 5.b.1, a fluid bed is constructed by means of the gas (G) and the fine final product of the sulfato compound, The entry temperature of the gas (G) used and the fluid bed temperature are chosen to be, for example, 200° C. 140° C. or 210° C./130° C. or 190° C./150° C. In contrast to the procedure of the batchwise preparation, in the continuous procedure the granules produced are removed parallel to the spraying of the reaction mixtures, as described in 5.a, continuously by means of the star wheel (14) so that the amount of granules present in the fluid bed remains constant. The particle size of the granules is controlled as in the batchwise procedure by metering in "fine final product" (sulfato compound) and/or by crushing the granules with the crusher (25) so that the process, owing to the constant amount of granules in the fluid bed and the constant particle size spectrum, takes place in the optimum "fluidized range".

6.c Results

On the basis of analyses of samples of granules which were removed during the spraying of the sulfuric acid solution or suspension of the sulfonyl starting compound from the fluid bed, it was determined that the esterification reaction (sulfation) during the spraying proceeds spontaneously and virtually completely so that no after reaction time ("heat treatment") is necessary. This was also confirmed by analyses of samples of granules which were subjected in the fluid bed at the reaction temperature chosen to a "heat treatment" of up to 3 hours and whose product composition with respect to the amount of sulfato final product underwent no more change. On average, the granules of the Examples with the gas entry and fluid bed temperatures shown in 6.b contained 98% of 2-bromo-4-(β-sulfatoethylsulfonyl)-aniline 1% of 2-bromo-4-(β-hydroxyethylsulfonyl)-aniline and 1% of 4-(β-sulfatoethylsulfonyl)-aniline, formed from 4-(β-hydroxyethylsulfonyl)-aniline, an impurity of the starting compound.

The virtually dust-free granules are distinguished, compared with products which were prepared in contact dryers, for example a drying pan, by a higher dissolution rate in an aqueous suspension upon addition of anhydrous sodium carbonate up to a pH of 7.

7. Preparation of 2,5-dimethoxy-4-(β-sulfatoethylsulfonyl)-aniline

7.a Preparation of the reaction mixtures

Technical grade water-moist or technical grade dry 2,5-dimethoxy-4-(β-hydroxyethylsulfonyl)-acetanilide is stirred into such an amount of aqueous sulfuric acid of 20 to 95% strength that the molar ratio between sulfonyl compound and sulfuric acid is, for example, 1:1 or 1:1.02 or 1:1.04. This gives, for example at 90° to 100° C., a solution, or at 20 to 25° C., a suspension which is fed into the convection dryer. Preferably those reaction mixtures are used which contain 50 to 68% of 2,5-dimethoxy-4-(β-hydroxyethylsulfonyl)-acetanilide and 16 to 23% of sulfuric acid (calculated as 100% strength).

7.b Process examples

7.b.1 Process principle

In a fluidized bed spray granulator (for example in accordance with FIG. 1), a fluid bed is constructed by means of the gas (G) and the fine final product, that is, 2,5-dimethoxy-4-(β-sulfatoethylsulfonyl)-aniline having a particle size, for example, smaller than or equal to 100 μm. The entry temperature of the gas (G) is chosen, for example, as described in Examples 7.b.2 to 7.b.5 and the fluid bed temperature (=reaction temperature) is kept constant as described in Examples 7.b.2 to 7.b.5 by continuously spraying one of the solutions or suspensions of the sulfonyl starting compound prepared in 7.a into the fluid bed. This produces granules in the fluid bed whose particle size is controlled by introducing fine final product of the sulfato compound and/or by crushing by means of crusher (25) and thus obtaining granules, for example, of 100 to 800 μm or 100 to 2,000 μm or 100 to 3,000 μm.

Example 7.b.2

The process is carried out, as described in process principle 7.b.1, using an entry temperature of the gas (G) of 200° C. and a fluid bed temperature (=reaction temperature) of 130°±5° C. This gives granules having the composition and grade characteristics as described in 7.c.

Example 7.b.3

The process is carried out, as described in process principle 7.b.1, using an entry temperature of the gas (G) of 220° C. and a fluid bed temperature (=reaction temperature) of 165°±5° C. This gives granules having the composition and grade characteristics as described in 7.c.

Example 7.b.4

The process is carried out, as described in process principle 7.b.1, using an entry temperature of the gas (G) of 180° C. and a fluid bed temperature (=reaction temperature) of 145° C. This gives granules having the composition and grade characteristics as described in 7.c.

Example 7.b.5

The process is carried out, as described in process principle 7.b.1, using an entry temperature of the gas (G) of 220° C. and a fluid bed temperature (=reaction temperature) of 150° C. This gives granules having the composition and grade characteristics as described in 7.c.

7.c Results

On the basis of analyses of samples of granules which were removed during the spraying of the sulfuric acid solution or suspension of the sulfonyl starting compound from the fluid bed, it was determined that the esterification reaction (sulfation) during the spraying proceeds spontaneously and virtually completely so that no afterreaction time ("heat treatment") is necessary. This has also confirmed by analyses of samples of granules which were subjected in the fluid bed at the reaction temperature chosen to a "heat treatment" of up to 2 hours and whose product composition with respect to the amount: of sulfato final product underwent no more change. On average, the granules of Examples 7.b.2 to 7.b.5 contained >96% of 2,5-dimethoxy-4-(β-sulfatoethylsulfonyl)-aniline, <2.5% of 2,5-dimethoxy-4-(β-hydroxyethylsulfonyl)-acetanilide and 0.3% of 2,5-dimethoxy-4-(β-hydroxyethylsulfonyl)-aniline.

The virtually dust-free granules are distinguished, compared with products which were prepared in contact dryers, for example a drying pan, by a higher dissolution rate in an aqueous suspension upon addition of anhydrous sodium carbonate up to a pH of 7.

8. Preparation of 2-methoxy-5-methyl-4-(β-sulfatoethylsulfonyl)-aniline

8.a Preparation of the reaction mixtures

Technical grade water-moist or technical grade dry 2-methoxy-5-methyl-4-(β-hydroxyethylsulfonyl)acetanilide is stirred into such an amount of aqueous sulfuric acid of 10 to 95% strength that the molar ratio between sulfonyl compound and sulfuric acid is, for example, 1:1 or 1:1.02 or 1:1.05. This gives, for example at 90° to 100° C., a solution, or at 20° to 25° C., a suspension which is fed into the convection dryer. Preferably those reaction mixtures are used which contain 37 to 55% of 2-methoxy- 5-methyl-4-(β-hydroxyethylsulfonyl)-acetanilide and 13 to 20% of sulfuric acid (calculated as 100% strength).

8.b Process examples

8.b.1 Process principle

In a fluidized bed spray granulator (for example in accordance with FIG. 1), a fluid bed is constructed by means of the gas (G) and the fine final product, that is, 2-methoxy-5-methyl-4-(β-sulfatoethylsulfonyl)-aniline having a particle size, for example, smaller than or equal to 100 μm. The entry temperature of the gas (G) is chosen, for example, as described in Examples 8.b.2 to 8.b.5 and the fluid bed temperature (=reaction temperature) is kept constant as described in Examples 8.b.2 to 8.b.5 by continuously spraying one of the solutions or suspensions of the sulfonyl starting compound prepared in 8.a into the fluid bed. This produces granules in the fluid bed whose particle size is controlled by introducing fine final product of the sulfato compound and/or by crushing by means of crusher (25) and thus obtaining granules, for example, of 100 to 800 μm or 100 to 200 μm or 100 to 3,000 μm.

Example 8.b.2

The process is carried out, as described in process principle 8.b.1, using an entry temperature of the gas (G) of 220° C. and a fluid bed temperature (=reaction temperature) of 165° C. This gives granules having the composition and grade characteristics as described in 8.c.

Example 8.b.3

The process is carried out, as described in process principle 8.b.1, using an entry temperature of the gas (G) of 200° C. and a fluid bed temperature (=reaction Temperature) of 145° C. This gives granules having the composition and grade characteristics as described in 8.c.

Example 8.b.4

The process is carried out, as described in process principle 8.b.1, using an entry temperature of the gas (G) of 180° C. and a fluid bed temperature (=reaction temperature) of 130° C. This gives granules having the composition and grade characteristics as described in 8.c,

Example 8.b,5

The process is carried out, as described in process principle 8.b.1, using an entry temperature of the gas (G) of 200° C. and a fluid bed temperature (=reaction temperature) of 155° C. This gives granules having the composition and grade characteristics as described in 8.c.

8.c Results

On the basis of analyses of samples of granules which were removed during the spraying of the sulfuric acid solution or suspension of the sulfonyl starting compound from the fluid bed, it was determined that the esterification reaction (sulfation) during the spraying proceeds spontaneously and virtually completely so that no afterreaction time ("heat treatment") is necessary. This was also confirmed by analyses of samples of granules which were subjected in the fluid bed at the reaction temperature chosen to a "heat treatment" of up to 4 hours and whose product composition with respect to the amount of sulfato final product underwent no change. On average, the granules of Examples 8.b.2 to 8.b.5 contained 92–96% of 2-methoxy-5-methyl-4-(β-sulfatoethylsulfonyl)-aniline, <0.4% of 2-methoxy-5-methyl-4-(β-hydroxyethylsulfonyl)-acetanilide and 2–5% of 2-methoxy-5-methyl-4-(β-hydroxyethylsulfonyl)-aniline and also 2–3% of byproducts which were contained in the technical grade starting compound due to its synthesis.

The virtually dust-free granules are distinguished, compared with products which were prepared in contact dryers, for example a drying pan, by a higher dissolution rate in an aqueous suspension upon addition of anhydrous sodium carbonate up to a pH of 7.

9. Preparation of 6-methoxy-3-(β-sulfatoethylsulfonyl)-aniline (sic)

9.a Preparation of the reaction mixtures

Technical grade water-moist or technical grade dry 2-methoxy-5-(β-hydroxyethylsulfonyl)-acetanilide is stirred into such an amount of aqueous sulfuric acid of 20 to 95% strength that the molar ratio between sulfonyl compound and sulfuric acid is, for example, 1:1.05 or 1:1.1 or 1:1.15. This gives, for example at 110°–115° C., a solution, or at 20° to 25° C., a suspension which is fed into the convection dryer.

Preferably those reaction mixtures are used which contain 50 to 65% of 2-methoxy-5-(β-hydroxyethylsulfonyl)-acetanilide and 19 to 26% of sulfuric acid (calculated as 100% strength).

9.b Process Examples

9.b.1 Process principle

In a fluidized bed spray granulator (for example in accordance with FIG. 1), a fluid bed is constructed by means of the gas (G) and the fine final product, that is, 2-methoxy-5-(β-sulfatoethylsulfonyl)-aniline having a particle size, for example, smaller than or equal to 100 μm. The entry temperature of the gas (G) is chosen, for example, as described in Examples 9.b.2 to 9.b.5 and the fluid bed-temperature (=reaction temperature) is kept constant as described in Examples 9.b.2 to 9.b.5 by continuously spraying one of the solutions or suspensions of the sulfonyl starting compound prepared in 9.a into the fluid bed. This produces granules in the fluid bed whose particle size is controlled by introducing fine final product of the sulfato compound and/or by crushing by means of crusher (25) and thus obtaining granules, for example, of 100 to 800 μm or 100 to 2,000 μm or 100 to 3,000 μm.

Example 9.b.2

The process is carried out, as described in process principle 9.b.1, using an entry temperature of the gas (G) of 200° C. and a fluid bed temperature (=reaction temperature) of 150° C. This gives granules having the composition and grade characteristics as described in 9.c.

Example 9.b.3

The process is carried out, as described in process principle 9.b.1, using an entry temperature of the gas (G) of 220° C. and a fluid bed temperature (=reaction temperature) of 165° C. This gives granules having the composition and grade characteristics as described in 9.c.

Example 9.b.4

The process is carried out, as described in process principle 9.b.1, using an entry temperature of the gas (G) of 180° C. and a fluid bed temperature (=reaction temperature) of 140° C. This gives granules having the composition and grade characteristics as described in 9.c.

Example 9.b.5

The process is carried out, as described in process principle 9.b.1, using an entry temperature of the the gas (G) of 200° C. and a fluid bed temperature (=reaction temperature) of 130° C. This gives granules having the composition and grade characteristics as described in 9.c.

9.c Results

On the basis of analyses of samples of granules which were removed during the spraying of the sulfuric acid solution or suspension of the sulfonyl starting compound from the fluid bed, it was determined that the esterification reaction (sulfation) during the spraying proceeds spontaneously and virtually completely so that no afterreaction time ("heat treatment") is necessary. This was also confirmed by analyses of samples of granules which were subjected in the fluid bed at the reaction temperature chosen to a "heat treatment" of up to 3 hours and whose product composition with respect to the amount of sulfato final product underwent no more change.

On average, the granules of Examples 9.b.2 to 9.b.5 contained

- 94–96% of 2-methoxy-5-(8-sulfatoethylsulfonyl)-aniline,
- 1–2.5% of 2-methoxy-5-(β-hydroxyethylsulfonyl)aniline
- 3.5% of unchanged byproducts which were contained in the technical grade starting compound due to its synthesis.

The virtually dust-free granules are distinguished, compared with products which were prepared in contact dryers, for example a drying pan, by a higher dissolution rate in an aqueous suspension upon addition of anhydrous sodium carbonate up to a OH of 7.

I claim:

1. A process for the preparation of a solid aminoaryl β-sulfatoethylsulfone compound in which an aminoaryl β-hydroxyethylsulfone starting compound is reacted with sulfuric acid in a sulfuric acid medium and the reaction mixture simultaneously dried which process is performed by spraying a reaction mixture consisting essentially of:

an aminoaryl β-hydroxyethylsulfone starting compound of the formula (2)

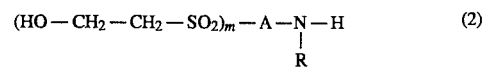

$$(HO-CH_2-CH_2-SO_2)_m-A-\underset{R}{N}-H \qquad (2)$$

in which m denotes the number 1 or 2, A is a phenylene or napththalene radical, both of which radicals are unsubstituted or substituted by 1, 2, or 3 alkyl groups of 1 to 4 carbon atoms, alkoxy groups of 1 to 4 carbon atoms, halogen, carboxyl, or hydroxyl, and R stands for a hydrogen atom or the acyl residue of a lower alkanecarboxylic acid, in 100% sulfuric acid or in an aqueous sulfuric acid having a water content of up to 90% by weight in a molar ratio of said starting compound to $H_2SO_4$ of about 1:1 to about 1:1.05, into a hot gas stream having a temperature of 150° to 360° C. of a fluidized bed spray granulator, a spray dryer, or a spray dryer having an integrated fluid bed, and recovering the solid, dry particles of a half-ester of the formula (1)

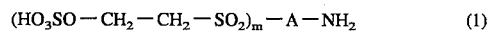

$$(HO_3SO-CH_2-CH_2-SO_2)_m-A-NH_2 \qquad (1)$$

where A and m are as defined previously, from said spray granulator or spray dryer.

2. The process as claimed in claim 1, which process comprises bringing the drying zone of a fluidized bed spray granulator, a spray dryer, or a spray dryer having an integrated fluid bed to an elevated temperature with said hot gas stream having a temperature of 150° to 360° C., conveying said reaction mixture, wherein said starting compound is essentially unesterified, to said drying zone, spraying said reaction mixture into said drying zone, said reaction mixture having a residence time in said drying zone which is short enough for continuous spraying of said reaction mixture into said drying zone and continuous discharge of reaction product from said drying zone, simultaneously carrying out drying and an esterification reaction in said drying zone at a said elevated temperature and recovering the resulting half-ester from said drying zone in the form of said dry particles.

3. The process as claimed in claim 1, wherein the sulfuric acid is an aqueous sulfuric acid.

4. The process as claimed in claim 1, wherein the drying and the reaction or reactions are carried out in a fluidized bed spray granulator in which the fluidized bed is produced pneumatically and/or mechanically.

5. The process as claimed in claim 1, wherein the drying and the reaction or reactions are carried out in said hot gas stream in a spray tower containing an atomizing disk or an atomizing nozzle.

6. The process as claimed in claim 1, wherein the drying and the reaction or reactions are carried out in a spray dryer having an integrated fluid bed.

7. The process as claimed in claim 1, wherein 4-(β-hydroxyethylsulfonyl)-acetanilide is converted to 4-(β-sulfatoethylsulfonyl)-aniline.

8. The process as claimed in claim 1, wherein 3-(β-hydroxyethylsulfonyl)aniline is converted to 3-(β-sulfatoethylsulfonyl)-aniline.

9. The process as claimed in claim 1, wherein 2-bromo-4-(β-hydroxyethylsulfonyl)-aniline is converted to 2-bromo-4-(β-sulfatoethylsulfonyl)aniline.

10. The process as claimed in claim 1, wherein 2-methoxy- 5-methyl-4-(β-hydroxyethylsulfonyl)acetanilide is converted to 2-methoxy-5-methyl-4-(β -sulfatoethylsulfonyl)-aniline.

11. The process as claimed in claim 1, wherein 2,5-dimethoxy- 4-(β-hydroxyethylsulfonyl)-acetanilide is converted to 2,5-dimethoxy-4-(β-sulfatoethylsulfonyl)-aniline.

12. The process as claimed in claim 1, wherein 2-methoxy- 5-(β-hydroxyethylsulfonyl)-acetanilide is converted to 2-methoxy-5-(β-sulfatoethylsulfonyl)aniline.

13. The process as claimed in claim 1, wherein said starting compound is in suspension or solution or in a paste.

14. The process as claimed in claim 1, wherein, in said formula (2), R is the acyl residue of a lower alkanecarboxylic acid, and hydrolysis of the N—R group of said formula (2) is carried out simultaneously with said drying and an esterification reaction.

15. The process as claimed in claim 2, wherein the sulfuric acid is an aqueous sulfuric acid.

16. The process as claimed in claim 2, wherein the drying and the reaction or reactions are carried out in a reaction zone containing a fluidized bed.

17. The process as claimed in claim 2, wherein the drying and the reaction or reactions are carried out in said hot gas stream in a spray tower containing an atomizing disk or an atomizing nozzle.

18. The process as claimed in claim 2, wherein said starting compound is in suspension or solution or in a paste.

19. The process as claimed in claim 2, wherein, in said formula (2), R is the acyl residue of a lower alkanecarboxylic acid, and hydrolysis of the NH—R group of said formula (2) is carried out simultaneously with said drying and said esterification reaction.

* * * * *